US005445611A

United States Patent [19]
Eppstein et al.

[11] Patent Number: 5,445,611
[45] Date of Patent: Aug. 29, 1995

[54] ENHANCEMENT OF TRANSDERMAL DELIVERY WITH ULTRASOUND AND CHEMICAL ENHANCERS

[75] Inventors: Jonathan A. Eppstein, Atlanta, Ga.; Deborah A. Eppstein, Salt Lake City, Utah

[73] Assignee: Non-Invasive Monitoring Company (NIMCO), Atlanta, Ga.

[21] Appl. No.: 152,174

[22] Filed: Dec. 8, 1993

[51] Int. Cl.⁶ .................................. A61M 37/00
[52] U.S. Cl. ........................... 604/49; 604/290
[58] Field of Search ........................ 604/20–23, 604/289–290, 49; 601/2; 606/1; 128/24

[56] References Cited

U.S. PATENT DOCUMENTS

| | | |
|---|---|---|
| 4,372,296 | 2/1983 | Fahim . |
| 4,646,725 | 3/1987 | Moasser . |
| 4,767,402 | 8/1988 | Kost et al. . |
| 4,780,212 | 10/1988 | Kost et al. . |
| 4,821,740 | 4/1989 | Tachibana et al. . |
| 4,953,565 | 9/1990 | Tachibana et al. . |
| 5,007,438 | 4/1991 | Tachibana et al. . |
| 5,016,615 | 5/1991 | Driller . |
| 5,171,215 | 12/1992 | Flanagan . |
| 5,231,975 | 8/1993 | Bommannan et al. . |
| 5,267,985 | 12/1993 | Shimada et al. . |

*Primary Examiner*—C. Fred Rosenbaum
*Assistant Examiner*—Perry E. Van Over
*Attorney, Agent, or Firm*—Thorpe, North & Western

[57] ABSTRACT

A method of enhancing the permeability of the skin or mucosa to a biologically active permeant or drug is described utilizing ultrasound or ultrasound plus a chemical enhancer. If desired the ultrasound may be modulated by means of frequency modulation, amplitude modulation, phase modulation and/or combinations thereof. A frequency modulation from high to low develops a local pressure gradient directed into the body, thus permitting permeant to traverse the skin or mucosa. The enhanced delivery is preferably accomplished using a chemical enhancer, applying ultrasound optionally at a modulated frequency, amplitude, phase, or combinations thereof that further induces a local pressure gradient into the body. The method is also useful as a means for application of a tattoo by noninvasively delivering a pigment through the skin surface.

33 Claims, 5 Drawing Sheets

ENHANCEMENT OF TRANSDERMAL DELIVERY WITH ULTRASOUND AND CHEMICAL ENHANCERS

BACKGROUND OF THE INVENTION

This invention relates generally to the field of drug delivery. More particularly, this invention relates to a non-invasive method of increasing the permeability of skin and other membranes through ultrasound or a combination of ultrasound and chemical enhancers for selectively enhancing transdermal and/or transmucosal drug delivery into the body.

The stratum corneum is chiefly responsible for the well known barrier properties of skin. Thus, it is this layer that presents the greatest barrier to transdermal flux of drugs or other molecules into the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermis cells, that lose their nuclei and become corneocytes. These dead cells then form the stratum corneum, which has a thickness of only about 10–20 $\mu$m and, as noted above, is a very resistant waterproof membrane that protects the body from invasion by exterior substances and the outward migration of fluids and dissolved molecules. The stratum corneum is continuously renewed by shedding of corneum cells during desquamination and the formation of new corneum cells by the keratinization process.

The flux of a drug or analyte across the skin can be increased by changing either the resistance (the diffusion coefficient) or the driving force (the gradient for diffusion). Flux may be enhanced by the use of so-called penetration or chemical enhancers. Chemical enhancers are well known in the art and a more detailed description will follow.

Other methods of increasing the permeability of skin to drugs have been described, such as ultrasound or iontophoresis. Iontophoresis involves the application of an external electric field and topical delivery of an ionized form of drug or an unionized drug carried with the water flux associated with ion transport (electro-osmosis). While permeation enhancement with iontophoresis has been effective, control of drug delivery and irreversible skin damage are problems associated with the technique.

Ultrasound has also been used to enhance permeability of the skin and synthetic membranes to drugs and other molecules. Ultrasound has been defined as mechanical pressure waves with frequencies above 20 kHz, H. Lutz et al., *Manual Of Ultrasound* 3–12 (1984). Ultrasound is generated by vibrating a piezoelectric crystal or other electromechanical element by passing an alternating current through the material, R. Brucks et al., 6 *Pharm. Res.* 697 (1989). The use of ultrasound to increase the permeability of the skin to drug molecules has been termed sonophoresis or phonophoresis.

U.S. Pat. No. 4,309,989 to Fahim describes topical application of medications in a coupling agent for the treatment of Herpes virus infections and demidox mite infestations. The medications are massaged into the affected area concurrently with application of ultrasound to cause the medication to penetrate the skin.

U.S. Pat. No. 4,372,296 to Fahim similarly describes treatment of acnes by topical application of zinc sulfate and ascorbic acid in a coupling agent.

U.S. Pat. No. 4,767,402 to Kost et al. discloses a method for enhancing and controlling infusion of molecules having a low rate of permeability through skin using ultrasound in the frequency range of between 20 kHz and 10 MHz, and in the intensity range of between 0 and 3 W/cm$_2$. The molecules are either incorporated in a coupling agent or, alternatively, applied through a transdermal patch. Kost et al. further teach that the parameters of time, frequency, and power can be optimized to suit individual situations and differences in permeability of various molecules and of various skins. U.S. Pat. No. 4,780,212 to Kost et al. teaches use time, intensity, and frequency control to regulate the permeability of molecules through polymer and biological membranes. Further, the choice of solvents and media containing the molecules also affects permeation of the molecules through the membranes. Transbuccal drug delivery with ultrasound has also been disclosed, U.S. Pat. No. 4,948,587 to Kost et al.

U.S. Pat. No. 5,115,805 to Bommannan et al. discloses the use of specific frequencies of ultrasound to enhance the rate of permeation of drugs through human skin. Frequencies above 10 MHz gave improved penetration of the skin above that described earlier. It is alleged but not shown that chemical penetration enhancers and/or iontophoresis could be used in connection with the ultrasound treatment.

U.S. Pat. No. 5,016,615 to Driller et al. involves local application of a medication by implanting a drug-containing receptacle adjacent to a body tissue to be treated and then applying ultrasound to drive the drug out of the receptacle and into the body tissue. This method has the disadvantage of requiring surgical implantation of the drug receptacle and a noninvasive technique is preferred. U.S. Pat. No. 4,821,740 to Tachibana et al. discloses a kit for providing external medicines that includes a drug-containing layer and an ultrasonic oscillator for releasing the drugs for uptake through the surface of the skin. In U.S. Pat. No. 5,007,438 to Tachibana et al. is described an application kit in which a layer of medication and an ultrasound transducer are disposed within an enclosure. The transducer may be battery powered. Ultrasound causes the medication to move from the device to the skin and then the ultrasound energy can be varied to control the rate of administration through the skin.

Other references teaching use of ultrasound to deliver drugs through the skin include D. Bommannan et al., 9 Pharmaceutical Res. 559 (1992); D. Bommannan et al., 9 Pharmaceutical Res. 1043 (1992); K. Tachibana, 9 Pharmaceutical Res. 952 (1992); P. Tyle & P. Agrawala, 6 Pharmaceutical Res. 355 (1989); H. Benson et al., 8 Pharmaceutical Res. 1991); Do Levy et al., 83 J. Clin. Invest. 2074 (1989).

Permeation through the stratum corneum can occur by (a) intracellular penetration, (b) intercellular penetration, and (c) transappendageal penetration, especially through the sebaceous pathway of the pilosebaceous apparatus and the aqueous pathway of the salty sweat glands. The utility of ultrasound in enhancing the permeability of the stratum corneum and, consequently, increasing transdermal flux rate is thought to derive from thermal and mechanical alteration of biological tissues. The parameters of ultrasound that are manipulable to improve or control penetration include frequency, intensity, and time of exposure. All three of these parameters may be modulated simultaneously in a complex fashion to increase the effect or efficiency of the ultrasound as it relates to enhancing the transdermal molecular flux rate either into or out of the human body. Other factors also play a part, for example the composition and structure of the membrane through which molecules are to be transported, the physical and chemical characteristics of the medium in which the molecules are suspended, and the nature of the molecules themselves. Since ultrasound is rapidly attenuated in air, a coupling agent, preferably one having lowest realizable absorption coefficient that is non-staining, nonirritating, and slow drying, may be needed to efficiently transfer the ultrasonic energy from the ultrasound transducer into the skin. When a chemical enhancer fluid or anti-irritant or both are employed, they may function as the coupling agent. For example, glycerin used as an anti-irritant may also function as a coupling agent. If needed, additional components may be added to the enhancer fluid to increase the efficiency of ultrasonic transduction. In general, ultrasound exposure times for permeation through human skin have been less than 60 minutes, preferably less than 10 minutes. It has been suggested that the maximum limit of exposure should be determined by monitoring skin temperature. However, monitoring of skin surface temperature would not necessarily monitor events such as rupture of cell membranes by mechanical shear forces which could occur at low temperatures with short duration, high intensity ultrasound. The exposure may be either continuous or pulsed to reduce heating of biological membranes. Average intensities have been in the range of 0.01-5 $W/cm^2$ and are selected to be high enough to achieve the desired result and low enough to avoid significant elevation of skin temperature. Frequencies have varied from 20 kHz to 50 MHz, preferably 5-30 MHz. The depth of penetration of ultrasonic energy into living soft tissue is inversely proportional to the frequency, thus high frequencies have been suggested to improve drug penetration through the skin by concentrating the effect in the outermost skin layer, the stratum corneum. Various refractive and/or reflective ultrasonic focusing systems may also be employed to concentrate the ultrasonic energy in the desired tissue independent of the fundamental frequency. When appropriate phase conditions are met, resonance of the system can be induced to favor higher frequency harmonic components of the fundamental ultrasonic energy, causing local zones of ultrasonic energy at 2, 3, 4 or more times the fundamental frequency.

Thus, while the use of ultrasound for drug delivery is known, results have been largely disappointing in that enhancement of permeability has been relatively low. There is no consensus on the efficacy of ultrasound for increasing drug flux across the skin. While some studies report the success of sonophoresis, J. Davick et al., 68 *Phys. Ther.* 1672 (1988); J. Griffin et al., 47 *Phys. Ther.* 594 (1967); J. Griffin & J. Touchstone, 42 *Am. J. Phys. Med.* 77 (1963); J. Griffin et al., 44 *Am. J. Phys. Med.* 20 (1965); D. Levy et al., 83 *J. Clin. Invest.* 2074); D. Bommannan et al., 9 *Pharm. Res.* 559 (1992), others have obtained negative results, H. Benson et al., 69 *Phys. Ther.* 113 (1988); J. McElnay et al., 20 *Br. J, Clin. Pharmacol.* 4221 (1985); H. Pratzel et al., 13 *J. Rheumatol.* 1122 (1986). Systems in which rodent skin were employed showed the most promising results, whereas systems in which human skin was employed have generally shown disappointing results. It is well known to those skilled in the art that rodent skin is much more permeable than human skin, and consequently the above results do not teach one skilled in the art how to effectively utilize sonophoresis as applied to transdermal delivery and/or monitoring through human skin.

In view of the foregoing problems and/or deficiencies, the development of a method for safely enhancing the permeability of the skin for transdermal delivery of drugs to a greater extent than can be achieved passively, and/or providing greater control over delivery rates and/or timing would be a significant advancement in the art.

Tattoos for both surgical and general use have traditionally been applied with one or more needles mounted in instruments or pens that may be hand held for dipping of the exposed needles in an appropriate solution containing pigment. Then the needles are used to puncture the skin so that the pigment is deposited subdermally. One improvement, described in U.S. Pat. No. 4,798,582 to Sarath et al., provided continuous delivery of pigment solution from a storage cartridge. Representative examples of electrical tattooing machines include U.S. Pat. Nos. 4,644,952; 4,508,106; 4,204,438; 4,159,659; and 4,031,783.

OBJECTS AND SUMMARY OF THE INVENTION

An object of the present invention is to provide a method for controlling transdermal and/or transmucosal flux rates of drugs or other molecules into the body and, if desired, into the bloodstream.

Another object of the invention is to controllably deliver drugs across the skin through minute perforations in the stratum corneum.

A further object of the invention is to provide a method for noninvasively applying tattoos to the skin.

These and other objects may be accomplished by applying various ultrasound frequencies to the skin, optionally with frequency, intensity and/or phase modulation, to control the direction and magnitude of the transdermal flux rate. Near field ultrasound energy patterns are characterized by a complex distribution of local energy peaks and nulls in the x, y, and z directions. By shifting the frequency with a frequency modulation, these fine patterns also shift, causing localized, but evenly distributed movement of pressure peaks and nulls in the z axis, i.e., the direction of propagation. As the frequency is modulated from a higher frequency to a lower frequency the peak energy concentration shifts from the head of the transducer at the skin surface toward the deeper layers of the skin due to the relationship between the differing penetration range of the various frequencies and the acoustic impedance of the various tissues. Therefore, by controlling the modulation parameters, ultrasonic enhancement of transdermal flux can be selectively optimized into the body.

Another aspect of the invention is the simultaneous use of chemical enhancers and ultrasound, optionally with modulated frequencies, amplitudes and/or phases, to lower lag times of penetration of chemical enhancers through the stratum corneum and increase transdermal flux rates of selected permeants. Ultrasound energy may be used to force chemical enhancers and associated permeants into the stratum corneum, thereby reducing the lag time associated with passive diffusion. Ultrasound energy also may open up diffusional pathways in the stratum corneum, thereby increasing permeability of that layer. Ultrasound energy also can serve to enhance the flux of active permeant molecules through the skin and other biological membranes by providing an active energy source, in addition to passive diffusion, to push or pump molecules through pores and channels.

A further aspect of the invention is the use of ultrasound energy, optionally with modulations of frequency, intensity and/or phase, to controllably push and/or pump molecules through the stratum corneum via perforations introduced by needle puncture, hydraulic jet, laser, electroporation, or other methods. By modulating intensity and/or frequency of the ultrasound energy, the transdermal flux rate through perforations is additionally regulated.

Still another aspect of the invention is the use of multiple ultrasound transducers to selectively direct the direction of transdermal flux into the body. Transducers may be placed on either side of a fold of flesh, such as an ear lobe, or in a pattern on a single dermal or mucosal surface and be selectively energized or energized in a phased fashion or energized at separate specific frequencies, intensities and/or phases or energized with separating frequencies, amplitude and/or phase modulations to control transdermal flux in the desired direction and at the desired rate.

Yet another aspect of the invention is the use of ultrasound reflectors and/or lenses to focus or otherwise control the distribution of ultrasound energy in the skin. By judicious placement of one or more reflectors and/or lenses, directional control of transdermal flux may be achieved by manipulating ultrasound frequency and intensity parameters.

A further aspect of the invention is the use of transdermal permeation methodology including but not limited to ultrasound (optionally with frequency, intensity and/or phase modulation), iontophoresis (optionally with current pulsing and/or modulation), chemical enhancers, or combinations thereof, to make tattoos on skin. In one application of this invention, a template of a pattern to be applied to the skin is made on a substrate with appropriate inks, dyes, or pigments and the like. The substrate or an absorbent pad placed adjacent to (e.g., on top of) the substrate is then saturated with appropriate chemical enhancers, placed next to the skin, and ultrasound energy is applied to transfer the pigments from the template on the substrate through the stratum corneum to the underlying dermis. The target area of the skin may be pretreated with ultrasound energy or chemical enhancers or both to increase effectiveness. Removable tattoos may be obtained with selected dyes, pigments, or inks and the like or combinations thereof, with removal effected by application of the appropriate enhancer technologies to facilitate removal of the tatoo pigments.

The ultrasound, preferably frequency, intensity and/or phase modulated, and with or without the use of chemical enhancers, may be applied at a frequency range of between about 0.1 and 100 MHz with a range of between about 3 and 30 MHz being preferred.

The invention is not drawn to novel chemical permeation enhancers per se. It is possible that some enhancer systems will function better than others with any given permeant. However, any or all of the enhancer systems forming the state of the art are believed to be functional in the present invention and, undoubtedly, enhancers yet to be developed can also be utilized.

The manner in which ultrasound energy, optionally with frequency, amplitude and/or phase modulation, and chemical enhancers are used concurrently for the delivery of permeants such as drugs and/or dyes form the basis for the invention as claimed.

DETAILED DESCRIPTION OF THE INVENTION

Although the present invention, as described herein, presents the best embodiment presently known for enhancing the transdermal flux rate of a drug or analyte through a biological membrane and enhancing the permeability of membranes using ultrasound, it is to be understood that this invention is not limited to the particular process steps and materials disclosed herein as such process steps and materials may, of course, vary. It is also to be understood that the terminology used herein is used for the purpose of describing particular embodiments only and is not intended to be limiting since the scope of the present invention will be limited only by the appended claims and their equivalents.

As used herein, "penetration enhancement" or "permeation enhancement" means an increase in the permeability of skin to a drug or chemical molecule (also called "permeant"), i.e., so as to increase the rate at which a drug or chemical molecule permeates through the skin either into the body or out of the body. The enhanced permeation effected through the use of such enhancers can be observed, for example, by observing diffusion of a dye, as a permeant, through animal or human skin using a diffusion apparatus.

As used herein, "chemical enhancer", "penetration enhancer" and the like shall be inclusive of all enhancers which increase the flux of a permeant, analyte or other molecule across the skin limited only by functionality. In other words, all cell envelope disordering compounds and solvents and any other chemical enhancement agents are intended to be included.

As used herein, "transdermal" or "percutaneous" means passage of a permeant into and through the skin to achieve effective therapeutic blood levels or desired deep tissue levels.

While the invention is described herein primarily in terms of "transdermal" flux or transdermal flux rate (TFR), it will be appreciated by those skilled in the art that the present disclosed and claimed methods for increasing transdermal flux rate also encompass "transmucosal" flux using ultrasound.

"Transmucosal" is intended to mean passage of any given material through a mucosal membrane of a living organism. More specifically, "transmucosal" refers to passage of a material from the outside environment of the organism, through a mucous membrane, and into the organism. Transmucosal administration of a drug includes delivery of a drug through either the nasal, buccal, sublingual, or other oral mucosal tissue, or through rectal or vaginal mucosal tissue.

As used herein, the term "permeant", "drug" or "pharmacologically active agent" or any other similar term means any chemical or biological material or compound suitable for transdermal or transmucosal administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This invention is not drawn to novel permeants or to new classes of active agents. Rather it is limited to the mode of delivery of agents or permeants which exist in the state of the art or which may later be established as active agents and which are suitable for delivery by the present invention. Such substances include broad classes of compounds normally delivered into the body, including through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered, as can drugs of either high or low molecular weight.

As used herein, "effective" amount of a pharmacologically active agent means a sufficient amount of a compound to provide the desired local or systemic effect and performance at a reasonable benefit/risk ratio attending any medical treatment. An "effective" amount of a permeation enhancer as used herein means an amount selected so as to provide the desired increase in skin permeability and the desired depth of penetration, rate of administration, and amount of drug or pigment delivered.

As used herein, "carriers" or "vehicles" refer to carrier materials without significant pharmacological activity at the quantities used which are suitable for administration with other pharmaceutically active materials, and include any such materials known in the art, e.g., any liquid, gel, solvent, liquid diluent, solubilizer, or the like, that is nontoxic at the quantities employed and does not interact with the drug to be administered in a deleterious manner. Examples of suitable carriers for use herein include water, mineral oil, silicone, inorganic gels, aqueous emulsions, liquid sugars, waxes, petroleum jelly, and a variety of other oils and polymeric materials.

As used herein, a "biological membrane" is intended to mean a membrane material present within a living organism that separates one area of the organism from another and, in many instances, that separates the organism from its outer environment. Skin and mucous membranes are thus included.

As used herein, "individual" refers to both a human and an animal, to which the present invention may be applied.

As used herein, "dye" or "pigment" or "ink" means any chemical or biological compound that is suitable for use in making a tattoo.

As used herein, "transdermal flux rate" is the rate of passage of any drug, pharmacologically active agent, dye, or pigment through the skin of an individual, human or animal.

As used herein, the terms "intensity amplitude", "intensity" and "amplitude" are used synonymously and refers to the amount of energy being produced by the ultrasound system.

Figure 4A:
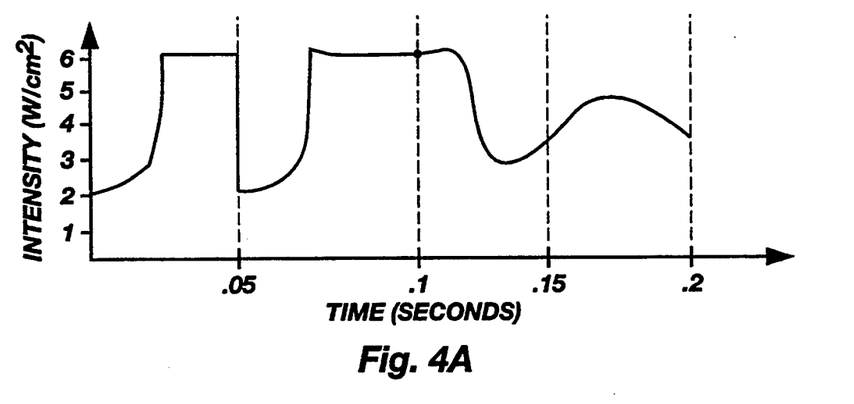
FIG. 4A shows an example of intensity modulation according to the present invention.
Figure 4B:
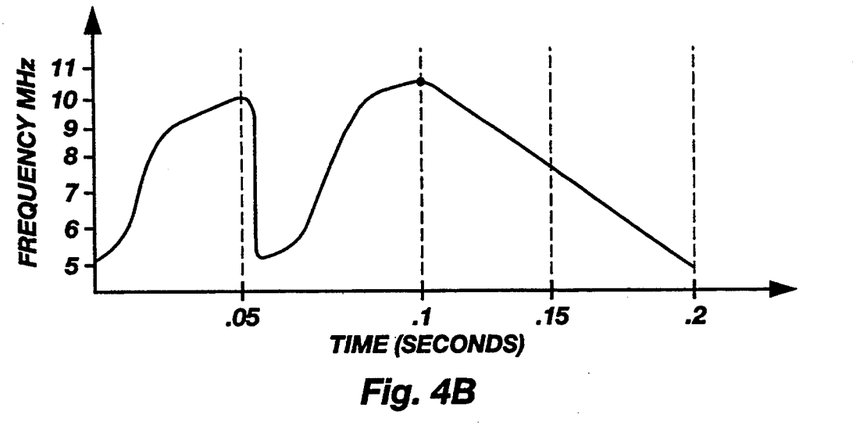
FIG. 4B shows an example of frequency modulation according to the present invention.

As used herein, "modulation" or "sweep" means variation in the amplitude or frequency of ultrasound in a given time period. A frequency modulation is a graded or stepped variation in frequency in a given time period, for example 5.4–5.76 MHz in 1 sec., or 5–10 MHz in 0.1 sec., or 10–5 MHz in 0.1 sec., or any other frequency range or time period that is appropriate to a specific application. A complex modulation may include varying both the frequency and intensity simultaneously. For example, FIGS. 4A and 4B could, respectively, represent amplitude and frequency modulations being applied simultaneously to a single ultrasonic transducer.

Figure 4C:
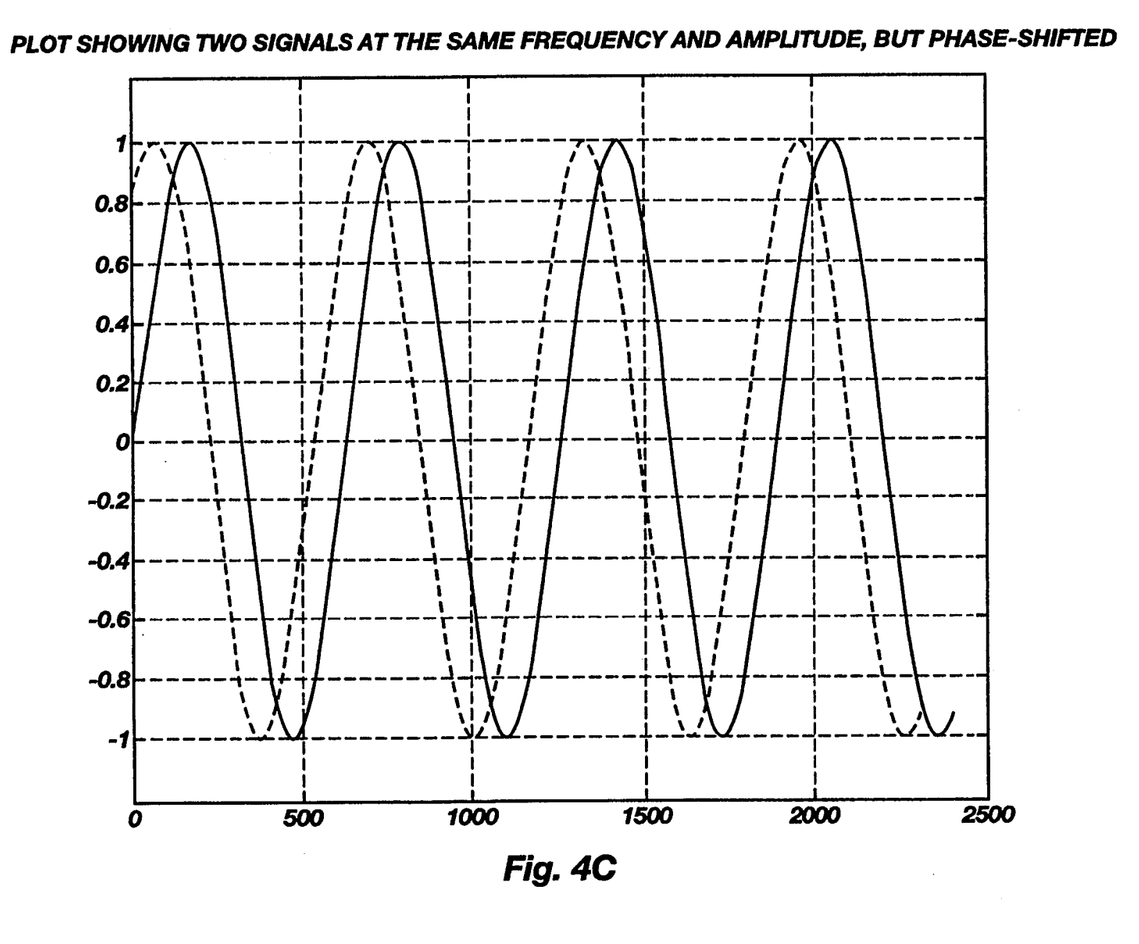
FIG. 4C shows an example of phase modulation according to the present invention.

As used herein "phase modulation" means the timing of the signal has been changed relative to its initial state shown in FIG. 4C. The frequency and amplitude of the signal may remain the same. A phase modulation can be implemented with a variable delay such as to selectively retard or advance the signal temporarily in reference to its previous state, or to another signal.

As used herein, "non-invasive" means not requiring the entry of a needle, catheter, or other invasive medical instrument into a part of the body.

Figure 1:
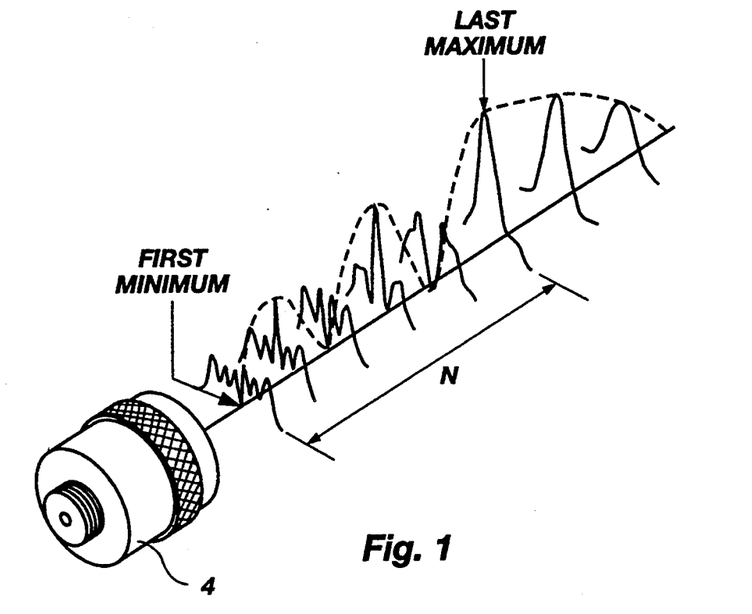
FIG. 1 shows the distribution of energy fields produced by an ultrasound transducer and division into near and far energy fields.

The physics of ultrasound energy fields created by ultrasound transducers may be utilized in a method by which ultrasound frequency can be modulated to improve on flux rates achieved by other methods. As shown in FIG. 1, the energy distribution of an ultrasonic transducer 4 may be divided into near and far fields. The near field, characterized by length N, is the zone from the first energy minimum to the last energy maximum. The zone distal to the last maximum is the far field. The near (N) field pattern is dominated by a large number of closely spaced local pressure peaks and nulls. The length of the near field zone, N, is a function of the frequency, size and shape of the transducer face, and the speed of sound in the medium through which the ultrasound travels. For a single transducer, intensity variations within its normal operating range do not affect the nature of the sonic energy distribution other than in a linear fashion. However, for a system with multiple transducers, all being modulated in both frequency and amplitude, the relative intensities of separate transducers do affect the energy distribution in the sonic medium, regardless of whether it is skin or another medium.

By changing the frequency of the ultrasound by a modest amount, for example in the range of about 1% to 20%, the pattern of peaks and nulls remains more or less constant in a relative fashion, but the length N of the near field zone changes in direct proportion to the frequency. Changing the frequency by a large amount, say a factor of 2 or more, will most likely produce a different set of resonances or vibrational modes in the transducer, causing a significantly and unpredictably different near field energy pattern. Thus, with a modest change in the frequency of the ultrasound, the complex pattern of peaks and nulls is compressed or expanded in an accordion-like manner. By selecting the direction of frequency modulation, the direction of shift of these local pressure peaks can be controlled. By applying ultrasound at the surface of the skin, selective modulation of the ultrasound frequency controls movement of these local pressure peaks through the skin either toward the interior of the body or toward the surface of the body. A frequency modulation from high to low drives the pressure peaks into the body, whereas a frequency modulation from low to high pulls the pressure peaks from within the body toward the surface.

Assuming typical parameters for this application of, for example, a 1.27 cm diameter ultrasound transducer, a nominal operating frequency of 10 MHz and an acoustic impedance similar to that of water, a frequency modulation of 1 MHz produces a movement of about 2.5 mm of the peaks and nulls of the near field energy pattern in the vicinity of the stratum corneum. From the perspective of transdermal and/or transmucosal drug delivery, this degree of action provides access to the area well below the stratum corneum and even the epidermis, dermis, and other tissues beneath it. For any given transducer, there may be an optimal range of frequencies within which this frequency modulation is most effective.

The ultrasound, in its various applications such as with frequency, intensity or phase modulation, or combinations thereof and the use of chemical enhancers combined with modulated ultrasound, as described herein, may vary over a frequency range of between about 0.1 to 100 MHz with a range of between about 3 and 30 MHz being preferred.

The flux of a drug or analyte across the skin can be increased by changing either the resistance (the diffusion coefficient) or the driving force (the gradient for diffusion). Flux may be enhanced by the use of so-called penetration or chemical enhancers.

Chemical enhancers are comprised of two primary categories of components, i.e., cell-envelope disordering compounds and solvents or binary systems containing both cell-envelope disordering compounds and solvents.

Cell envelope disordering compounds are known in the art as being useful in topical pharmaceutical preparations and function also in analyte withdrawal through the skin. These compounds are thought to assist in skin penetration by disordering the lipid structure of the stratum corneum cell-envelopes. A comprehensive list of these compounds is described in European Patent Application 43,738, published Jun. 13, 1982, which is incorporated herein by reference. It is believed that any cell envelope disordering compound is useful for purposes of this invention. Exemplary of the cell envelope disordering compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH$_3$, COOCH$_2$CH(OR'')CH$_2$OR'', —(OCH$_2$CH$_2$)$_m$OH, —COOR', or —CONR'$_2$ where R' is —H, —CH$_3$, —C$_2$H$_5$, —C$_2$H$_7$ or —C$_2$H$_4$OH; R'' is -H, or a non-terminal alkenyl of about 7 to 22 carbon atoms; and m is 2–6; provided that when R'' is an alkenyl and X is —OH or —COOH, at least one double bond is in the cis-configuration.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European Patent Application 43,738, referred to above, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is also incorporated herein by reference.

A binary system for enhancing metaclopramide penetration is disclosed in UK Patent Application GB 2,153,223 A, published Aug. 21, 1985, and consists of a monovalent alcohol ester of a C8–32 aliphatic monocarboxylic acid (unsaturated and/or branched if C18–32) or a C6–24 aliphatic monoalcohol (unsaturated and/or branched if C14–24) and an N-cyclic compound such as 2-pyrrolidone, N-methylpyrrolidone and the like.

Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C$_2$ to C$_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Other chemical enhancers, not necessarily associated with binary systems, include DMS0 or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems may possess negative side effects such as toxicity and skin irritation. U.S. Pat. No. 4,855,298 discloses compositions for reducing skin irritation caused by chemical enhancer-containing compositions having skin irritation properties with an amount of glycerin sufficient to provide an anti-irritating effect.

Because it is the combination of ultrasound accompanied by the use of chemical enhancers that result in the improved rate of permeant or drug delivery through the stratum corneum, the specific carrier vehicle and particularly the chemical enhancer utilized may be selected from a long list of prior art vehicles some of which are mentioned above and incorporated herein by reference. To specifically detail or enumerate that which is readily available in the art is not thought necessary. The invention is not drawn to the use of chemical enhancers per se and it is believed that all chemical enhancers, useful in the delivery of drugs through the skin, will function with ultrasound in further enhancing the delivery of permeants or drugs through the skin surface.

Figure 2:
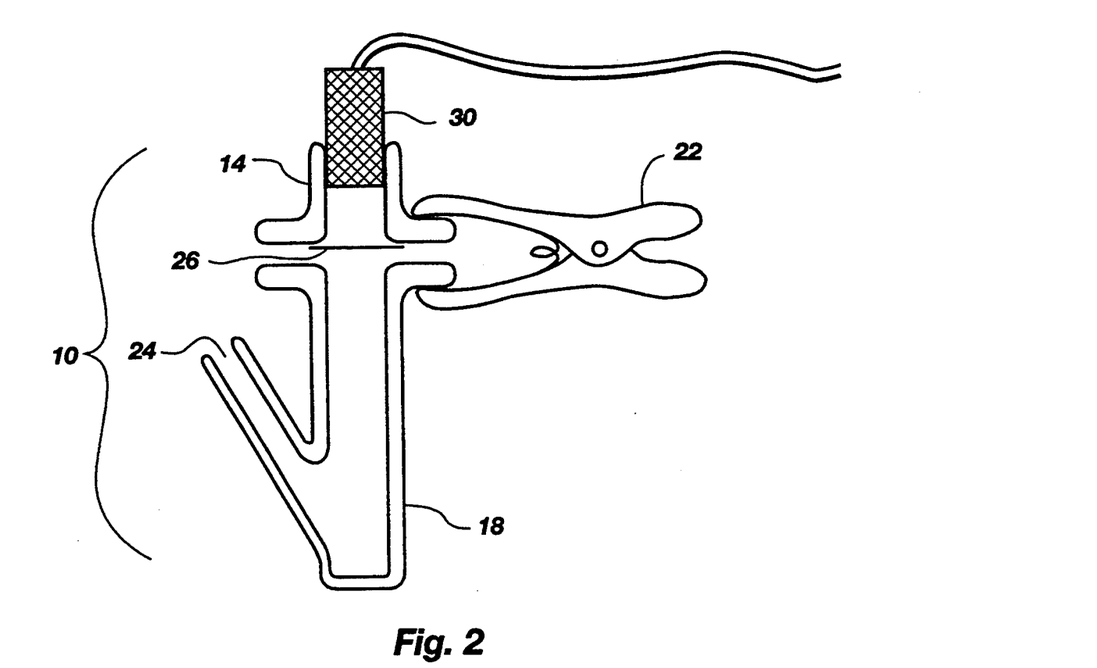
FIG. 2 shows a modified Franz cell used in testing the invention.

Modulated ultrasound and chemical enhancers were tested for their ability to control transdermal flux on human cadaver skin samples. In the tests conducted the epidermal membrane had been separated from the human cadaver whole skin by the heat-separation method of Klineman and Christopher (*Arch. Dermatol.* 88:702 (1963)) involving the exposure of the full thickness skin to 60° C. heat for 60 seconds, after which time the stratum corneum and part of the epidermis (epidermal membrane) were gently peeled off the dermis. The epidermal membrane was cut and placed between two halves of the permeation cell with the stratum corneum facing either the upper (donor) compartment or lower (receiver) compartment. Modified Franz cells were used to hold the epidermis, as shown in FIG. 2. Each Franz cell 10 consists of an upper chamber 14 and a lower chamber 18 held together with one or more clamps 22. The lower chamber 18 has a sampling port 24 through which materials may be added or removed. A sample of stratum corneum 26 is held between the upper 14 and lower 18 chambers when they are clamped together. The upper chamber 14 of each Franz cell 10 is modified to allow an ultrasound transducer 30 to be positioned within 1 cm of the stratum corneum membrane 26. Methylene blue solution was used as an indicator molecule to assess the permeation of the stratum corneum. A visual record of the process and results of each experiment was obtained in a time stamped magnetic tape format with a video camera and video cassette recorder (not shown). Additionally, samples were withdrawn for measurement with an absorption spectrometer to quantitate the amount of dye which had traversed the stratum corneum membrane during an experiment. Chemical enhancers suitable for use could vary over a wide range of solvents and/or cell envelope disordering compounds. The specific enhancer utilized was: ethanol/glycerol/water/glycerol monooleate/methyl laurate in 50/30/15/2.5/2.5 volume ratios. The system for producing and controlling the ultrasound energy included a programmable 0–30 MHz arbitrary waveform generator, a 20 watt 0–30 MHz amplifier, and two unfocused ultrasound immersion transducers having peak resonances at 15 and 25 MHz, respectively. Six cells were prepared simultaneously for testing of stratum corneum samples from the same donor. Once the stratum corneum samples were installed, they were allowed to hydrate with distilled water for at least 6 hours before any tests were done.

Effects of Ultrasound without Chemical Enhancers

As stated above, the heat-separated epidermis was placed in the Franz cells with the epidermal side facing up, and the stratum corneum side facing down, unless noted otherwise. The lower chambers were filled with distilled water, whereas the upper chambers were filled with concentrated methylene blue solution in distilled water.

EXAMPLE 1

Heat Separated Epidermis

Immediately after filling the upper chambers with methylene blue solution, ultrasound was applied to one of the cells with the transducer fully immersed. This orientation would correspond, for example, to having the transducer on the opposite side of a fold of skin, or causing the ultrasound to be reflected off a reflector plate similarly positioned and being used to 'push' analyte out of the other side of the fold into a collection device. The ultrasound setting was initially set at the nominal operating frequency of 25 MHz with an intensity equivalent to a 20 volt peak-to-peak (P—P) input wave form. This corresponds to roughly a 1 watt of average input power to the transducer and similarly, assuming the manufacturer's nominal value for conversion efficiency of 1% for this particular transducer, a sonic output power of around 0.01 watts over the 0.78 $cm^2$ surface of the active area or an ultrasonic intensity of 0.13 watts/$cm^2$. Three other control cells had no ultrasound energy applied to them. After 5 minutes the ultrasound was turned off. No visual indication of dye flux across the stratum corneum was observed during this interval in any of the cells, indicating levels less than approximately 0.0015% (v/v) of dye solution in 2 ml of receiver medium.

Testing of these same 3 control cells and 1 experimental cell was continued as follows. The intensity of ultrasound was increased to the maximum possible output available from the driving equipment of a 70 volt peak-to-peak input 12 watts average power input or ($\approx$0.13 watts/$cm^2$) of ultrasonic output intensity. Also, the frequency was set to modulate or sweep from 30 MHz to 10 MHz. This 20 MHz sweep was performed ten times per second, i.e., a sweep rate of 10 Hz. At these input power levels, it was necessary to monitor the ultrasound transducer to avoid overheating. A contact thermocouple was applied to the body of the transducer and power was cycled on and off to maintain maximum temperature of the transducer under 42° C. After about 30 minutes of cycling maximum power at about a 50% duty cycle of 1 minute on and 1 minute off, there was still no visually detectable permeation of the stratum corneum by the methylene blue dye.

A cooling water jacket was then attached to the ultrasound transducer to permit extended excitation at the maximum energy level. Using the same 3 controls and 1 experimental cell, ultrasound was applied at maximum power for 12 hours to the experimental cell. During this time the temperature of the fluid in the upper chamber rose to only 35° C., only slightly above the approximately 31° C. normal temperature of the stratum corneum in vivo. No visual evidence of dye flux through the stratum corneum was apparent in any of the four cells after 12 hrs. of ultrasound applied as described above.

EXAMPLE 2

Perforated Stratum Corneum

Six cells were prepared as described above. The clamps holding the upper and lower chambers of the Franz cells were tightened greater than the extent required to normally seal the upper compartment from the lower compartment, and to the extent to artificially introduce perforations and "pinholes" into the heat-separated epidermal samples. When dye solution was added to the upper chamber of each cell, there were immediate visual indications of leakage of dye into the lower chambers through the perforations formed in the stratum corneum. Upon application of ultrasound to cells in which the stratum corneum was so perforated with small "pinholes," a rapid increase in the transport of fluid through a pinhole in the stratum corneum was observed. The rate of transport of the indicator dye molecules was directly related to whether the ultrasound was applied or not. That is, application of the ultrasound caused an immediate (lag time approximately <0.1 second) pulse of the indicator molecules through the pinholes in the stratum corneum. This pulse of indicator molecules ceased immediately upon turning off of the ultrasound (a shutoff lag of approximately <0.1 second). The pulse could be repeated as described.

Effects of Ultrasound and chemical Enhancers

Two different chemical enhancer formulations were used. Chemical Enhancer One or CE1 was an admixture of ethanol/glycerol/water/glycerol monooleate/methyl laurate in a 50/30/15/2.5/2.5 volume ratio. These are components generally regarded as safe, i.e. GRAS, by the FDA for use as pharmaceutical excipients. Chemical Enhancer Two or CE2 is an experimental formulation shown to be very effective in enhancing transdermal drug delivery, but generally considered too irritating for long term transdermal delivery applications. CE2 contained ethanol/glycerol/water/lauradone/methyl laurate in the volume ratios 50/30/15/2.5/2.5. Lauradone is the lauryl (dodecyl) ester of 2-pyrrolidone-5-carboxylic acid ("PCA") and is also referred to as lauryl PCA.

EXAMPLE 3

Six Franz cells were set up as before except that the heat separated epidermis was installed with the epidermal layer down, i.e., stratum corneum side facing up. Hydration was established by exposing each sample to distilled water overnight. To begin the experiment, the distilled water in the lower chambers was replaced with methylene blue dye solution in all six cells. The upper chambers were filled with distilled water and the cells were observed for about 30 minutes confirming no passage of dye to ensure that no pinhole perforations were present in any of the cells. When none were found, the distilled water in the upper chambers was removed from four of the cells. The other two cells served as distilled water controls. The upper chambers of two of the experimental cells were then filled with CE1 and the other two experimental cells were filled with CE2.

Ultrasound was immediately applied to one of the two CE2 cells. A 25 MHz transducer was used with the frequency sweeping every 0.1 second from 10 MHz to 30 MHz at maximum intensity of $\approx 0.13$ watts/cm$^2$. After 10-15 minutes of ultrasound applied at a 50% duty cycle, dye flux was visually detected. No dye flux was detected in the other five cells.

Ultrasound was then applied to one of the two cells containing CE1 at the same settings. Dye began to appear in the upper chamber within 5 minutes. Thus, ultrasound together with a chemical enhancer significantly increased the transdermal flux rate of a marker dye through the stratum corneum, as well as reduced the lag time.

EXAMPLE 4

Formulations of the two chemical enhancers were prepared minus the glycerin and these new formulations, designated CE1MG and CE2MG, were tested as before. Water was substituted for glycerin so that the proportions of the other components remained unchanged. Three cells were prepared in modified Franz cells with the epidermal side of the heat separated epidermis samples facing toward the upper side of the chambers. These samples were then hydrated in distilled water for 8 hours. After the hydration step, the distilled water in the lower chambers was replaced with either CE1MG or CE2MG and the upper chamber was filled with the dye solution. Ultrasound was applied to each of the three cells sequentially.

Upon application of pulsed, frequency-modulated ultrasound for a total duration of less than 10 minutes, a significant increase in permeability of the stratum corneum samples was observed. The permeability of the stratum corneum was altered relatively uniformly across the area exposed to both the chemical enhancer and ultrasound. No "pinhole" perforations through which the dye could traverse the stratum corneum were observed. The transdermal flux rate was instantly controllable by turning the ultrasound on or off. Turning the ultrasound off appeared to instantly reduce the transdermal flux rate such that no dye was visibly being actively transported through the skin sample; presumably the rate was reduced to that of passive diffusion. Turning the ultrasound on again instantly resumed the high level flux rate. The modulated mode appeared to provide a regular pulsatile increase in the transdermal flux rate at the modulated rate. When the ultrasound was set to a constant frequency, the maximum increase in transdermal flux rate for this configuration seemed to occur at around 27 MHz.

Having obtained the same results with all three samples, the cells were then drained of all fluids and flushed with distilled water on both sides of the stratum corneum. The lower chambers were then immediately filled with distilled water and the upper chambers were refilled with dye solution. The cells were observed for 30 minutes. No holes in the stratum corneum samples were observed and no large amount of dye was detected in the lower chambers. A small amount of dye became visible in the lower chambers, probably due to the dye and enhancer trapped in the skin samples from their previous exposures. After an additional 12 hours, the amount of dye detected was still very small.

EXAMPLE 5

Perforated Stratum Corneum

Three cells were prepared with heat-separated epidermis samples with the epidermal side facing toward the upper side of the chamber from the same donor as in Example 4. The samples were hydrated for 8 hours and then the distilled water in the lower chambers was replaced with either CE1MG or CE2MG. The upper chambers were then filled with dye solution. Pinhole perforations in the stratum corneum samples permitted dye to leak through the stratum corneum samples into the underlying enhancer containing chambers. Ultrasound was applied. Immediately upon application of the ultrasound, the dye molecules were rapidly pushed through the pores. As in example 2, the rapid flux of the dye through the pores was directly and immediately correlated with the application of the ultrasound.

EXAMPLE 6

A low cost ultrasound transducer, TDK #NB-58S-01 (TDK Corp.), was tested for its capability to enhance transdermal flux rates. The peak response of this transducer was determined to be about 5.4 MHz with other local peaks occurring at about 7 MHz, 9 MHz, 12.4 MHz, and 16 MHz.

This TDK transducer was then tested at 5.4 MHz for its ability to enhance transdermal flux rate in conjunction with CE1MG. Three cells were set up with the epidermal side facing the lower chamber, then the skin samples were hydrated for 8 hrs. The dye solution was placed in the lower chamber. The transducer was placed in the upper chamber immersed in CE1MG. Using swept frequencies from 5.3 to 5.6 MHz as the ultrasound excitation, significant quantities of dye moved through the stratum corneum and were detected in the collection well of the cell in 5 minutes. Local heating occurred, with the transducer reaching a temperature of 48° C. In a control using CE1MG without ultrasound, a 24 hour exposure yielded less dye in the collection well than the 5 minute exposure with ultrasound.

This example demonstrates that a low cost, low frequency ultrasound transducer can strikingly affect transdermal flux rate when used in conjunction with an appropriate chemical enhancer. Although higher frequency ultrasound will theoretically concentrate more energy in the stratum corneum, when used with a chemical enhancer, the lower frequency modulated ultrasound can accelerate the transdermal flux rate to make the technology useful and practical.

EXAMPLE 7

Demonstration of Molecule Migration Across Human Skin

Figure 3A:
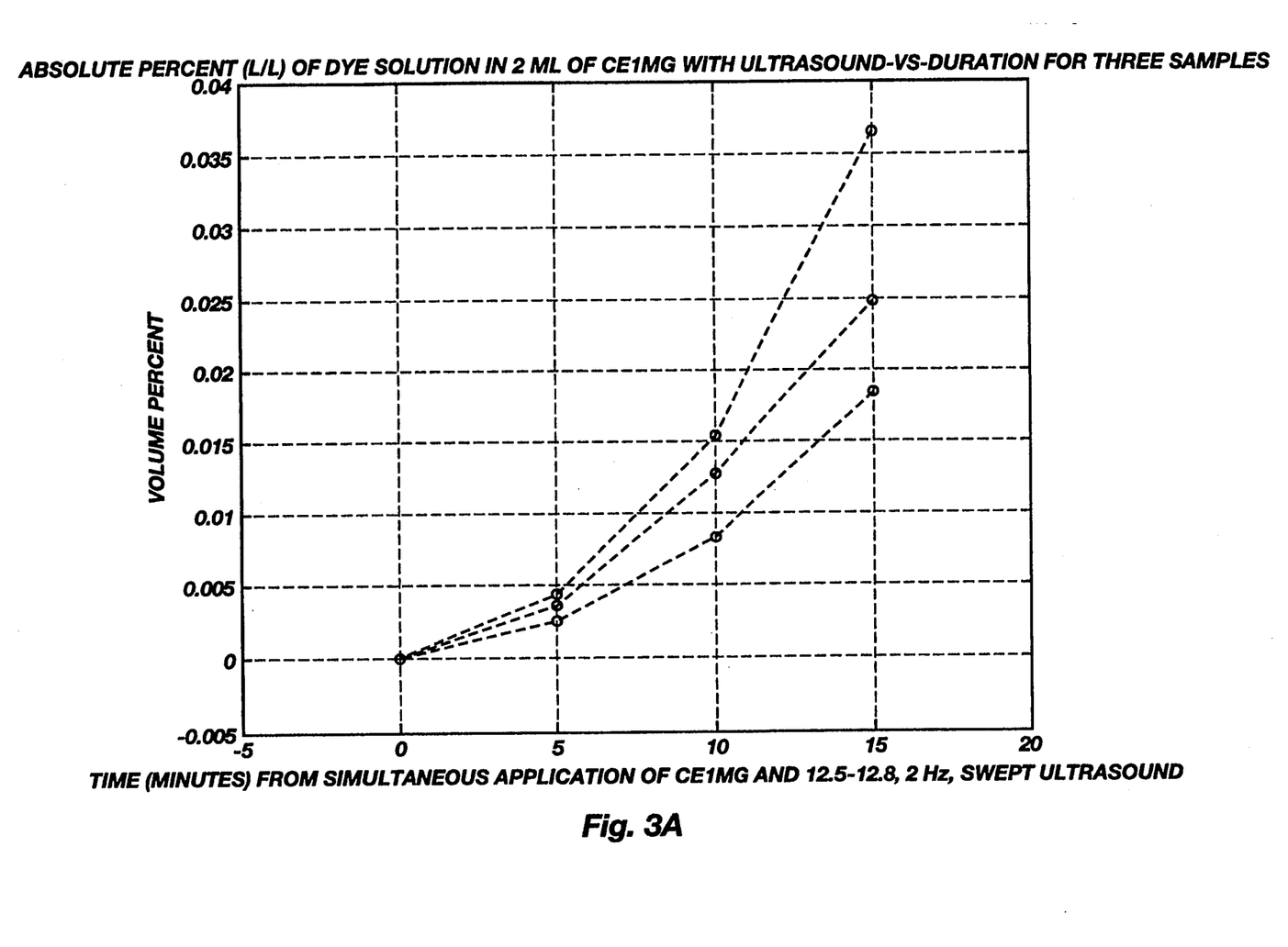
FIG. 3A shows one embodiment of dye flux across human skin obtained using ultrasound in conjunction with a chemical enhancer.
Figure 3B:
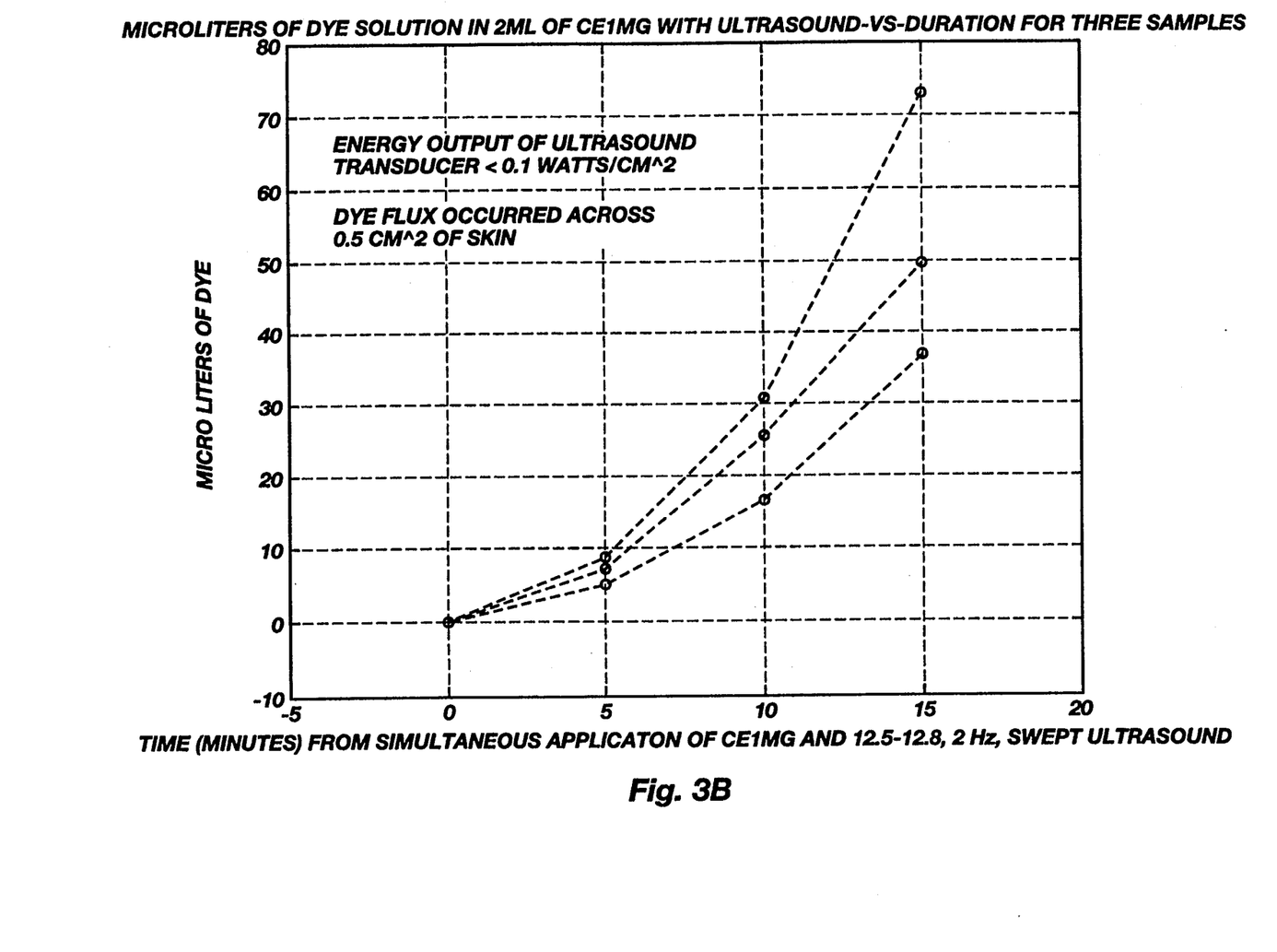
FIG. 3B shows another embodiment of dye flux across human skin obtained using ultrasound in conjunction with a chemical enhancer.

Tests with the TDK transducer and CE1MG described in Example 6 were repeated at about 12.4 MHz, one of the highest local resonant peaks for the transducer, with a frequency sweep at a 2 Hz rate from 12.5 to 12.8 MHz and an ultrasonic energy density less than 0.1 W/cm$^2$. The epidermal side of the heat-separated epidermis was facing down, the dye solution was in the lower chamber, and the enhancer solution and the ultrasound were placed in the upper chamber. The results of this experiment are shown in FIGS. 3A and 3B. Within 5 minutes a significant amount of dye had moved across the stratum corneum into the collection well. Ohmic heating in the transducer was significantly less than with the same transducer being driven at 5.4 MHz, causing an increase in temperature of the chemical enhancer to only about 33° C.

Even at these low efficiency levels, the results obtained with CE1MG and ultrasound from the TDK transducer were remarkable. FIGS. 3A and 3B show plots of data obtained from three separate cells. Even at the 5 minute time point, readily measurable quantities of the dye were present in the collection well.

Ultrasound and CE1MG enhanced delivery of dye through 5 different skin samples showed that, after about 4.5–5.5 minutes of simultaneously applied chemical enhancer and ultrasound, the dye began flooding through the stratum corneum. This shift in permeability from virtually zero to very permeable occurred over about a 20 second interval. When the ultrasound was turned off, the TFR reverted to a much lower rate, comparable to the standard passive diffusion TFR typically associated with transdermal drug delivery systems utilizing this chemical enhancer formulation.

EXAMPLE 8

The following are exemplary of representative formulations containing active agents or permeants and chemical enhancers that can be used within the scope of the invention. However, they are illustrative only and are not intended to define the scope of the invention. All compositions are in percent by weight. PEG 400 and PPG 2000 refer, respectively, to polyethylene glycol of average molecular weight 400 and polypropylene glycol of average molecular weight 2000.

| FORMULATION 8-A | | |
|---|---|---|
| Testosterone | | 5–15% |
| Enhancer | | 85–95% |
| Glycerol dioleate | 5–90% | |
| Ethanol | 5–49% | |
| PEG 400 | 0–45% | |
| FORMULATION 8-B | | |
| Methadone | | 10–30% |
| Enhancer | | 70–90% |
| Glycerol dioleate | 20 | |
| Ethanol | 49 | |
| PEG 400 | 31 | |
| FORMULATION 8-C | | |
| Estradiol | | 0.1–1.0% |
| Enhancer | | 99–99.9% |
| Glycerol dioleate | 10 | |
| Ethanol | 49 | |
| PEG 400 | 41 | |
| FORMULATION 8-D | | |
| Ketoprofen | | 10–20% |
| Enhancer | | 80–90% |
| Glycerol dioleate | 40% | |
| Ethanol | 40% | |
| PPG 2000 | 20% | |
| FORMULATION 8-E | | |
| Dihydroergotamine | | 1–10% |
| Enhancer | | 90–99% |
| Glycerol dioleate | 40% | |
| Ethanol | 40% | |
| PEG 400 | 20% | |
| FORMULATION 8-F | | |
| Nifedapine | | 2–10% |
| Enhancer | | 90–98% |
| Glycerol dioleate | 45% | |
| Ethanol | 10% | |

|                        |       |         |
|------------------------|-------|---------|
| Mineral oil            | 45%   |         |
| FORMULATION 8-G    |       |         |
| Thiethylperazine       |       | 1–5%    |
| Enhancer               |       | 95–99%  |
|   Glycerol dioleate | 10% |      |
|   Ethanol    | 45%   |         |
|   PEG 400    | 45%   |         |
| FORMULATION 8-H    |       |         |
| Metoclopramide         |       | 10–15%  |
| Enhancer               |       | 85–90%  |
|   Glycerol dioleate | 30% |      |
|   Ethanol    | 25%   |         |
|   PPG 2000   | 45%   |         |
| FORMULATION 8-I    |       |         |
| Propranolol HCl        |       | 5%      |
| Enhancer               |       | 95%     |
|   Glycerol dioleate | 60% |      |
|   Ethanol    | 20%   |         |
|   PEG 400    | 20%   |         |
| FORMULATION 8-J    |       |         |
| Propranolol            |       | 20%     |
| Enhancer               |       | 80%     |
|   Glycerol dioleate | 70% |      |
|   Ethanol    | 20%   |         |
|   PPG 2000   | 10%   |         |
| FORMULATION 8-K    |       |         |
| Fentanyl citrate       |       | 2%      |
| Enhancer               |       | 98%     |
|   Glycerol monooleate | 6% |     |
|   Ethanol    | 49%   |         |
|   H$_2$O     | 45%   |         |
| FORMULATION 8-L    |       |         |
| Fentanyl               |       | 1%      |
| Enhancer               |       | 99%     |
|   Glycerol trioleate | 15% |     |
|   Isopropanol | 45%  |         |
|   Mineral oil | 40%  |         |
| FORMULATION 8-M    |       |         |
| Nicardipine            |       | 5%      |
| Enhancer               |       | 95%     |
|   Oleyl alcohol | 10% |         |
|   Isopropanol | 45%  |         |
|   PPG 2000   | 45%   |         |
| FORMULATION 8-N    |       |         |
| Nicardipine HCl        |       | 10%     |
| Enhancer               |       | 90%     |
|   Oleic acid | 2%    |         |
|   Glycerol dioleate | 10% |      |
|   Ethanol    | 45%   |         |
|   PEG 400    | 43%   |         |
| FORMULATION 8-O    |       |         |
| Naloxone HCl           |       | 10%     |
| Enhancer               |       | 90%     |
|   Glycerol monooleate | 5% |     |
|   Oleic acid | 2%    |         |
|   Ethanol    | 49%   |         |
|   H$_2$O     | 44%   |         |
| FORMULATION 8-P    |       |         |
| Griseofulvin           |       | 5%      |
| Enhancer               |       | 95%     |
|   Glycerol trioleate | 50% |     |
|   Isopropanol | 15%  |         |
|   PPG 2000   | 35%   |         |
| FORMULATION 8-Q    |       |         |
| Fluocinolone actonide  |       | 1%      |
| Enhancer               |       | 99%     |
|   Glycerol trioleate | 80% |     |
|   Isopropanol | 10%  |         |
|   Mineral oil | 10%  |         |
| FORMULATION 8-R    |       |         |
| Clindamycin            |       | 2.5%    |
| Enhancer               |       | 97.5%   |
|   Oleyl alcohol | 40% |         |
|   Isopropanol | 30%  |         |
|   Mineral oil | 30%  |         |
| FORMULATION 8-S    |       |         |
| Neomycin sulfate       |       | 5%      |
| Enhancer               |       | 95%     |
|   Glycerol monooleate | 6% |     |
|   Ethanol    | 49%   |         |
|   H$_2$O     | 45%   |         |
| FORMULATION 8-T    |       |         |
| Clonidine HCl          |       | 1%      |
| Enhancer               |       | 99%     |
|   Glycerol dioleate | 10% |      |
|   Ethanol    | 45%   |         |
|   PEG 400    | 45%   |         |
| FORMULATION 8-U    |       |         |
| Hydroflumethiazide     |       | 10%     |
| Enhancer               |       | 90%     |
|   Glycerol dioleate | 10% |      |
|   Oleic acid | 5%    |         |
|   Isopropanol | 45%  |         |
|   PEG 400    | 40%   |         |
| FORMULATION 8-V    |       |         |
| Phentermine            |       | 5%      |
| Enhancer               |       | 95%     |
|   Glycerol trioleate | 60% |     |
|   Propanol   | 10%   |         |
|   Mineral oil | 30%  |         |
| FORMULATION 8-W    |       |         |
| Mazindol               |       | 5%      |
| Enhancer               |       | 95%     |
|   Glycerol trioleate | 40% |     |
|   Isopropanol | 20%  |         |
|   PPG 2000   | 40%   |         |
| FORMULATION 8-X    |       |         |
| Morphine sulfate       |       | 5%      |
| Enhancer               |       | 95%     |
|   Glycerol monooleate | 6% |     |
|   Oleic acid | 4%    |         |
|   Ethanol    | 45%   |         |
|   PEG 400    | 45%   |         |
| FORMULATION 8-Y    |       |         |
| Alprazolam             |       | 5%      |
| Enhancer               |       | 95%     |
|   Glycerol trioleate | 60% |     |
|   Propanol   | 20%   |         |
|   Mineral oil | 20%  |         |
| FORMULATION 8-Z    |       |         |
| Ibuprofen              |       | 10%     |
| Enhancer               |       | 90%     |
|   Glycerol trioleate | 20% |     |
|   Isopropanol | 49%  |         |
|   PPG 2000   | 31%   |         |
| FORMULATION 8-AA   |       |         |
| Naproxen sodium        |       | 10%     |
| Enhancer               |       | 90%     |
|   Glycerol dioleate | 40% |      |
|   Oleyl alcohol | 5%  |         |
|   Ethanol    | 25%   |         |
|   PEG 400    | 30%   |         |
| FORMULATION 8-BB   |       |         |
| Progesterone           |       | 5%      |
| Enhancer               |       | 95%     |
|   Oleyl alcohol | 25% |         |
|   Isopropanol | 30%  |         |
|   PEG 400    | 45%   |         |
| FORMULATION 8-CC   |       |         |
| Methyl testosterone    |       | 5%      |
| Enhancer               |       | 95%     |
|   Glycerol trioleate | 40% |     |
|   Isopropanol | 40%  |         |
|   PPG 2000   | 20%   |         |

EXAMPLE 9

Similar to audible sound, ultrasound waves can undergo reflection, refraction, and absorption when they encounter another medium with dissimilar properties [D. Bommannan et al., 9 Pharm. Res. 559 (1992)]. Reflectors or lenses may be used to focus or otherwise control the distribution of ultrasound energy in a tissue of interest. For many locations on the human body, a fold of flesh can be found to support this system. For example, an earlobe is a convenient location which would allow use of a reflector or lens to assist in exerting directional control (e.g., "pushing" of analytes through the stratum corneum) similar to what is realized by changing ultrasound frequency and intensity.

EXAMPLE 10

Multiple ultrasound transducers may be used to selectively direct transdermal flux into the body. Similar to the system described in Example 8, a fold of skin such as an earlobe allow transducers to be located on either side of the fold. The transducers may be energized selectively or in a phased fashion to enhance transdermal flux in the desired direction. An array of transducers or an acoustic circuit may be constructed to use phased array concepts, similar to those developed for radar and microwave communications systems, to direct and focus the ultrasonic energy into the area of interest.

EXAMPLE 11

Ultrasound and chemical enhancers may be used to noninvasively apply and/or remove tattoos to or from skin. In one embodiment of the invention, a piece of paper or other appropriate material is provided with ink, dye, or pigments disposed thereon in the desired pattern (template) and saturated with a suitable chemical enhancero The paper is then placed in contact with the skin at the location to which the tattoo is to be applied. Ultrasound is then applied to assist in permeabilizing the stratum corneum and driving the pigments therethrough and into the underlying dermis. Alternately, the skin may first be pre-treated with suitable chemical enhancers and ultrasound for a sufficient time to permeabilize the stratum corneum. The template is then placed on the pre-treated skin, and ultrasound is applied to drive the pigments into the skin. Alternately, rather than use of a template, the pigments may be applied directly to pretreated skin (i.e., painted or drawn on) in the desired pattern, protected if necessary by a suitable membrane, and then driven into the permeabilized skin via application of ultrasound. Alternately, the skin may first be pre-treated with a suitable chemical enhancer or enhancers and ultrasound for a sufficient time to permeabilize the stratum corneum, as a pre-treatment for conventional tattooing techniques to facilitate less traumatic and quicker placement of the tattoo pigments into the skin. Other means of transdermal permeation as are known in the art may also be employed to apply the tattoos. For example, iontophoresis or electroporation, either alone or combined with chemical enhancers, or ultrasound, or any appropriate combination of the various transdermal enhancement technologies, can be employed to apply pigments into the skin to achieve a tattoo. For removal of a tattoo, when pigments that enable removal were used in the tattoo, similar permeation enhancer technologies as described above are employed to facilitate noninvasive removal of the pigments from the skin.

The above examples and illustrated embodiments are but representative of systems which may be employed in the utilization of one or more enhancement means for the transdermal delivery of permeants, including pigments. The use of ultrasound with or without the use of chemical enhancers is particularly preferred. The invention is directed to the discovery that the proper use of ultrasound, particularly when accompanied with the use of chemical enhancers, enables the noninvasive transdermal or transmucosal delivery of permeants including pigments. However, the invention is not limited only to the specific illustrations. There are numerous enhancer systems some of which may function better than another for delivery of permeants. However, within the guidelines presented herein, a certain amount of experimentation to obtain optimal enhancers, or optimal time, intensity and frequency of applied ultrasound, as well as modulation of frequency, amplitude and phase of applied ultrasound can be readily carried out by those skilled in the art. Therefore, the invention is limited in scope only by the following claims and functional equivalents thereof.

We claim:

1. In a method for enhancing the transdermal flux rate of an active permeant into a selected area of an individual's body surface comprising the steps of (a) contacting the selected area with a composition comprising an effective amount of said permeant; and (b) enhancing the permeability of the selected area to the permeant by means of applying ultrasound to said selected area for a time and at an intensity and a frequency effective to enhance the transdermal flux rate into the body;

the improvement comprising; modulating said applied ultrasound by means of a member selected from the group consisting of frequency modulation, amplitude modulation, phase modulation and combinations thereof.

2. The method of claim 1 wherein the ultrasound is modulated by means of a member selected from the group consisting of frequency modulation and a combination of frequency and amplitude modulation.

3. The method of claim 2 wherein the ultrasound is frequency modulated.

4. The method of claim 1 wherein the ultrasound is amplitude modulated.

5. The method of claim 2 wherein the ultrasound has a frequency in the range of about 0.1 to 100 MHz.

6. The method of claim 5 wherein the ultrasound has a frequency in the range of about 3 to 30 MHz.

7. The method of claim 1 which further comprises using a plurality of transducers for applying said modulated ultrasound.

8. The method of claim 1 wherein said time is in the range of about 1 to 30 minutes.

9. The method of claim 2 wherein the frequency is applied in a sweeping modulation from a higher frequency to a lower frequency for a time sufficient to enable the permeant to penetrate the body surface.

10. The method of claim 1 wherein a chemical permeation enhancer is also applied to the selected surface area.

11. The method of claim 10 wherein the ultrasound is modulated by means of a member selected from the group consisting of frequency modulation and a combination of frequency and amplitude modulation.

12. The method of claim 10 wherein the ultrasound is frequency modulated.

13. The method of claim 12 wherein the ultrasound is amplitude modulated.

14. The method of claim 11 wherein the ultrasound has a frequency in the range of about 0.1 to 100 MHz.

15. The method of claim 14 wherein the ultrasound has a frequency in the range of about 3 to 30 MHz.

16. The method of claim 10 wherein the ultrasound has a frequency in the range of about 0.1 to 100 MHz.

17. The method of claim 10 further comprises using a plurality of transducers for applying said modulated ultrasound.

18. The method of claim 10 wherein said time is in the range of about 1 to 30 minutes.

19. The method of claim 11 wherein the frequency is applied in a sweeping modulation from a higher frequency to a lower frequency for a time sufficient to enable the permeant to penetrate the body surface.

20. A method for applying a tattoo to a selected area of skin on an individual's body surface comprising the steps of:
(a) contacting the selected area of skin with a pigment; and
(b) enhancing the permeability of the selected area to said pigment for a time sufficient to enable the pigment to penetrate through an outer layer of the body surface, wherein said enhancement is accomplished by application to the selected area of a means selected from the group consisting of ultrasound, chemical permeation enhancement, iontophoresis, electroporation, and combinations thereof.

21. The method of claim 20 wherein said enhancement is accomplished by means of the application of a chemical permeation enhancer.

22. The method of claim 20 wherein said enhancement is accomplished by means of the application of ultrasound.

23. The method of claim 20 wherein said enhancement is accomplished by means of the application of iontophoresis.

24. The method of claim 20 wherein said enhancement is accomplished by means of the application of electroporation.

25. The method of claim 21 wherein ultrasound is also applied.

26. The method of claim 25 wherein said ultrasound is modulated by means of a member selected from the group consisting of frequency modulation, amplitude modulation, phase modulation and combinations thereof.

27. The method of claim 26 wherein the ultrasound is modulated by means of a member selected from the group consisting of frequency modulation and a combination of frequency and amplitude modulation.

28. The method of claim 25 wherein the ultrasound is frequency modulated.

29. The method of claim 26 wherein the ultrasound is amplitude modulated.

30. The method of claim 26 which further comprises using a plurality of transducers for applying ultrasound.

31. The method of claim 27 wherein the frequency is applied in a sweeping modulation from a higher frequency to a lower frequency for a time sufficient to enable the permeant to penetrate the body surface.

32. The method of claim 20 wherein the dye is a permanent dye.

33. The method of claim 20 wherein the dye is a removable dye.

* * * * *